United States Patent [19]

LaHann et al.

[11] Patent Number: 4,544,669

[45] Date of Patent: Oct. 1, 1985

[54] COMPOUNDS AND COMPOSITIONS USEFUL FOR PRODUCING ANALGESIA

[75] Inventors: Thomas R. LaHann, Cleves; John M. Janusz, Fairfield, both of Ohio; Brian L. Buckwalter, Yardley, Pa.

[73] Assignee: The Procter & Gamble Company, Cincinnati, Ohio

[21] Appl. No.: 514,207

[22] Filed: Jul. 14, 1983

[51] Int. Cl.[4] .................... A01N 37/02; A01N 37/06; A01N 37/18; A61K 31/165
[52] U.S. Cl. .................................. 514/563; 260/404; 514/599; 514/613
[58] Field of Search ................ 260/404; 424/324, 311; 514/563, 599, 613

[56] References Cited

U.S. PATENT DOCUMENTS

| | | | |
|---|---|---|---|
| 3,268,582 | 8/1966 | Zeile et al. | |
| 3,558,500 | 1/1971 | Hollis et al. | 260/404 X |
| 3,621,043 | 11/1971 | Seki et al. | 260/404 |
| 3,741,999 | 6/1973 | Seki et al. | 260/404 |
| 3,803,185 | 4/1974 | Henrick et al. | 260/404 |
| 3,816,484 | 6/1974 | Henrick | 260/404 |
| 3,888,893 | 6/1975 | Siddall | 260/404 |
| 3,897,428 | 7/1975 | Omura et al. | 260/404 |
| 3,920,523 | 11/1975 | Lichtenwalter et al. | 260/404 |
| 4,238,508 | 12/1980 | Nelson | |
| 4,313,958 | 2/1982 | LaHann | 424/324 |
| 4,401,663 | 8/1983 | Buckwalter et al. | 424/321 |

OTHER PUBLICATIONS

Chemical Abstracts 75, 118128z (1971).
Ferris et al., "New Approach to Insecticidal Paints", *Aust. Commonwealth Dept. Supply Def. Stand. Lab.* Tech. Note No. 89 (1966) (*Chem. Abs.* 67: 22919s).
Kiernan, "A Study of Chemically Induced Acute Inflammation in the Skin of the Rat *Quart. J. Exp. Physiol.,* vol 62, (1977), pp. 151–161.
Jansco et al., "Direct Evidence for Neurogenic Inflammation and its Prevention by Denervation and by Pretreatment with Capsaicin," *Br. J. Pharm. Chemother.,* vol. 3 (1967), pp. 138–151.
Arvier, et al., "Modification by Capsaicin and Compound 4/80 of Dye Leakage Induced by Irritants in the Rat," *Br. J. Pharm.,* vol. 59, (1977), pp. 61–68.
Yaksh et al., "Intrathecal Capsaicin Depletes Substance P in the Rat Spinal Cord and Produces Prolonged Thermal Analgesia," *Science,* vol. 260, (1979), pp. 481–483.
Virus et al., "Pharmacologic Actions of Capsaicin: Apparent Involvement of Substance P and Serotonin," *Life Sciences,* vol. 24, (1979), pp. 1273–1281.
Jones et al., "The Relation Between Chemical Constitution and Pungency in Acid Amides," *J. Chem. Soc.,* vol. 27, (1925), pp. 2588–2598.
Newman, "Natural and Synthetic Pepper-Flavored Substances," *Chem. Prod.,* (Mar. 1954), pp. 102–106.
Szolesanyi et al., "Sensory Effects of Capsaicin Congeners," *Arzneim.-Forsch.,* vol. 25, (1975), pp. 1871–1881.
Szolesanyi et al., "Sensory Effects of Capsaicin Congeners," *Arzneim.-Forsch.,* vol. 26, (1976), pp. 33–37.
Hegyes et al., "Synthesis of Homovanillic Acid Derivatives of Capsaicin-Like Effect," *Acta. Phys. Chem.,* vol. 20, (1974), pp. 115–120.
Michalski et al., "Synthesis and Local Anesthetic Properties of N-Substituted 3,4-Dimethoxyphenethylamine Derivatives," *Diss. Pharm. Pharmacol.,* vol. 24, (1972) pp. 17–25 (*Chem. Abs.* 77: 19271a).
T. Szeki, "Contributions Towards Understanding the Relation Between the Chemical Constitution and the Sharp Taste of Acylamines," *Arch. Pharm.,* vol. 268, (1930), pp. 151–157.
Ott et al., *Liebigs Ann.* vol. 425 (1921), pp. 314–337.

*Primary Examiner*—Helen M. S. Sneed
*Attorney, Agent, or Firm*—David K. Dabbiere; Steven J. Goldstein; David L. Suter

[57] ABSTRACT

Alkadienamide compounds, and pharmaceutically-acceptable salts thereof, of the formula:

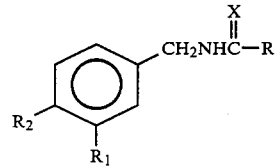

wherein X is O or S; R is straight or branched diene having from 11 to 23 carbon atoms; $R_1$ is H, OH, or $OCH_3$; $R_2$ is OH or a short-chain ester; and wherein at least one of $R_1$ and $R_2$ is OH or $OCH_3$. Compositions, useful for producing analgesia in humans or lower animals, comprise a safe and effective amount of: an alkadienamide, pharmaceutically-acceptable salts thereof, or mixtures thereof; and a pharmaceutically-acceptable carrier. Preferably, these alkadienamides are N-vanillylalkadienamides. Methods of treatment, comprising administering a safe and effective amount of these alkadienamides, pharmaceutically-acceptable salts thereof, or mixtures thereof, include methods of parenteral, oral, and topical administration.

22 Claims, No Drawings

COMPOUNDS AND COMPOSITIONS USEFUL FOR PRODUCING ANALGESIA

BACKGROUND OF THE INVENTION

This invention relates to compositions, containing certain N-phenylmethylalkenamides, having analgesic activity.

While "pain" is incapable of precise definition due to its basically subjective nature, it can generally be said that the term refers to feelings of distress or suffering caused by stimulation of specialized nerve endings. A great variety of drugs have been developed to reduce pain in man and other animals; some directed to eliminating pain at its source, and others directed to blocking the assimilation of pain by the brain. Among the latter group of drugs that are designed to block the sensation of pain, are the analgesics, which generally relieve pain without causing unconsciousness. Analgesics can be further classified in two main categories: opioid analgesics, including morphine, codeine, levorphanol, and the morphine-like analgesics meperidine, and methadone; and antipyretic analgesics, such as aspirin, phenacetin, acetaminophen, phenylbutazone, and indomethacin.

Although the precise pharmacological action of these analgesics is uncertain, there are certain effects which readily distinguish the opioid analgesics from the antipyretics. In particular, the antipyretics are weak analgesics, with much of their effect in the peripheral nervous system, so that behavioral changes do not usually occur. Generally, these analgesics relieve only somatic pain originating from muscles, joints, tendons and fasciae, and are ineffective against deep visceral pain. However, the opioid analgesics are quite effective against all types of pain, with broad based action in the central nervous system. Aside from potent analgesia, the opioids, also known as narcotics, often produce effects on mood and other behavioral changes. Perhaps the most notable side effect of the opioid analgesics is the fact that their repeated use is associated with tolerance as well as psychic and physical dependence.

It has been recently discovered that capsaicin, a natural product of certain species of the genus Capsicum, induces analgesia in animals. Capsaicin (8-methyl-N-vanillyl-6E-nonenamide) and "synthetic" capsaicin (N-vanillylnonanamide) are disclosed as analgesics in U.S. Pat. No. 4,313,958, LaHann, issued Feb. 2, 1982. Analgesic activity of capsaicin has also been discussed in the chemical and medical literature, including Yaksh, et al., *Science*, 206, 481–483 (1979). The use of capsaicin to prevent dipilatory irritation is also disclosed in U.S. patent application Ser. No. 330,731, LaHann, et al., filed Dec. 14, 1981.

Specifically, capsaicin prevents the development of cutaneous hyperalgesia and also provides relief of deep visceral pain and severe pain. In certain tests, capsaicin produces a level of analgesia comparable to morphine, yet it is not antagonized by such narcotic antagonists as nalorphine and naloxone. Thus, capsaicin does not appear to belong to either of the major categories of analgesics, described above.

Compounds structurally similar to capsaicin have been described in the chemical literature. These references, though, do not suggest analgesic activity for these compounds. For example, Newman, "Natural and Synthetic Pepper-Flavored Substances (6)," *Chemical Products*, 102–106 (1954) lists the relative pungency of approximately 164 compounds, including N-vanillyloleamide and other alkenamide derivatives of capsaicin. Ott and Zimmermann, *Liebigs Ann.*, 425, 314–337 (1921) discloses a synthesis for N-vanillyloleamide. A synthesis for N-vanillyllinoleamide is disclosed in Ferris, *Australian Commonwealth, Dep. Supply, Def. Stand. Lab.*, No. 89 (1966) (Chem. Abs. 67:22919).

U.S. Pat. No. 4,238,505, Nelson, issued Dec. 9, 1980, discloses 3-hydroxyacetanilide for use in producing analgesia in animals. U.S. patent application Ser. No. 359,464, LaHann, et al., filed Mar. 18, 1982 now U.S. Pat. No. 4,424,206, issued Jan. 3, 1984, describes hydroxyphenylacetamides with analgesic and anti-irritant activity. Similarly, analgesic and anti-irritant activity is disclosed for N-vanillylsulfonamides in U.S. patent application Ser. No. 360,953, Buckwalter, et al., filed Mar. 23, 1982 now U.S. Pat. No. 4,401,663, issued Aug. 30, 1983; N-vanillylureas in U.S. patent application Ser. No. 381,672, Buckwalter, et al., filed May 25, 1982 now U.S. Pat. No. 4,460,602, issued July 17, 1984; and N-vanillylcarbamates in U.S. patent application Ser. No. 384,685, Buckwalter, et al., filed June 3, 1982 now U.S. Pat. No. 4,443,473, issued Apr. 17, 1984.

It has now been discovered that certain N-phenylmethyl alkadienamides have analgesic activity in humans and lower animals. In particular, these alkenamides have potent analgesic activity similar to that of capsaicin, but are substantially less toxic.

SUMMARY OF THE INVENTION

The present invention provides compounds useful for producing analgesia in humans and lower animals, of the formula:

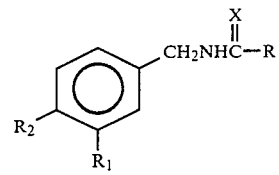

wherein X is O or S, R is straight or branched diene having from 11 to 23 carbon atoms, $R_1$ is H, OH, or $OCH_3$, $R_2$ is OH or a short-chain ester, wherein at least one of $R_1$ and $R_2$ is OH or $OCH_3$; and pharmaceutically-acceptable salts thereof.

This invention also provides compositions comprising a safe and effective amount of these compounds, or mixtures thereof, and a pharmaceutically-acceptable carrier. Also provided are methods for producing analgesia by administering the compounds and compositions of this invention.

DESCRIPTION OF THE INVENTION

The compositions and methods of this invention incorporate certain N-[(substituted phenyl)methyl]-diunsaturated amides (e.g., N-vanillyl-diunsaturated amides), or pharmaceutically-acceptable salts thereof, (herein "alkadienamides") of the formula:

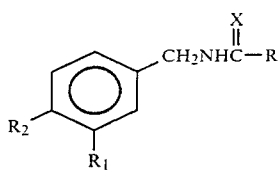

wherein X is O or S; R is straight or branched diene having from 11 to 23 carbon atoms; $R_1$ is H, OH or $OCH_3$; $R_2$ is OH or a short-chain ester; and wherein at least one of $R_1$ and $R_2$ is OH or $OCH_3$. R preferably contains from 16 to 21 carbon atoms and, preferably, unsaturated bonds are at position six or greater, i.e., wherein R is a (m,n-alkadiene), m is at least six. Also preferred are alkadienamides wherein X is O, alkadienamides wherein $R_1$ is $OCH_3$ and $R_2$ is OH, and alkadienamides wherein $R_2$ is a short-chain (i.e., $C_1$–$C_6$) ester, e.g., acetoxy.

Preferred alkadienamides include those where R is derived from such diunsaturated fatty acids as (Z,Z)-9,12-octadecadienoic (linoleic) acid, (E,E)-9-12-octadecadienoic (linoelaidic) acid, (Z,E)-9-12-octadecadienoic acid, (Z,E)-9,11-octadecadienoic acid, (E,E)-10,13-nonadecadienoic acid, and (E,E)-11,14-eicosadienoic acid. Preferred pharmaceutically-acceptable alkadienamide salts include the sodium, potassium, calcium, magnesium, and ammonium salts.

The alkadienamides described herein can be readily prepared by the following general synthetic scheme:

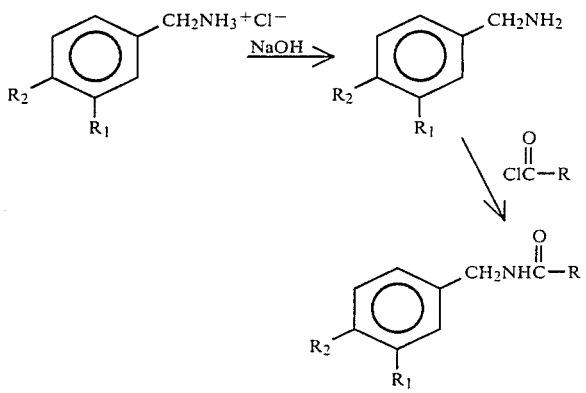

The fatty acids used in the synthesis of preferred alkadienamides are commercially-available.

Compositions

The compositions of the present invention comprise:
(a) a safe and effective amount of an alkadienamide; and
(b) a pharmaceutically-acceptable carrier.

A safe and effective amount of alkadienamide is that amount which provides analgesia, thereby alleviating or preventing the pain being treated at a reasonable benefit/risk ratio, as is intended with any medical treatment. Obviously, the amount of alkadienamide will vary with such factors as the particular condition that is being treated, the severity of the condition, the duration of the treatment, the physical condition of the patient, the nature of concurrent therapy (if any), the specific formulation and carrier employed, and the solubility and concentration of alkadienamide therein.

Depending upon the particular route of administration, a variety of pharmaceutically-acceptable carriers, well known in the art, may be used. These include solid or liquid fillers, diluents, hydrotropes, surface-active agents, and encapsulating substances. The amount of the carrier employed in conjunction with the alkadienamide is sufficient to provide a practical quantity of material per unit dose of analgesic.

Pharmaceutically-acceptable carriers for systemic administration, that may be incorporated into the compositions of this invention, include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Specific pharmaceutically-acceptable carriers are described in the following U.S. patent applications, all incorporated by reference herein: Ser. No. 359,464, LaHann, et al., filed Mar. 18, 1982 now U.S. Pat. No. 4,424,206, issued Jan. 3, 1984; Ser. No. 360,953, Buckwalter, et al., filed Mar. 23, 1982 now U.S. Pat. No. 4,401,663, issued Aug. 30, 1983; Ser. No. 381,672, Buckwalter, et al., filed May 25, 1982 now U.S. Pat. No. 4,460,602, issued July 17, 1984; and Ser. No. 384,685, Buckwalter, et al., filed June 3, 1982 now U.S. Pat. No. 4,443,473, issued Apr. 17, 1984. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

Various oral dosage forms can be used, including such solid forms as tablets, capsules, granules and bulk powders. These oral forms comprise a safe and effective amount, usually at least about 5%, and preferably from about 25% to about 50% of the alkadienamide. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules and effervescent preparations reconstituted from effervescent granules, containing suitable solvents, preservatives, emulsifying agents, suspending agents, diluents, sweeteners, melting agents, coloring, and flavoring agents. Preferred carriers for oral administration include gelatin, propylene glycol, cottonseed oil and sesame oil. Specific examples of pharmaceutically-acceptable carriers and excipients that may be used to formulate oral dosage forms, which may be used in formulating oral dosage forms containing alkadienamides, are described in U.S. Pat. No. 3,903,297, Robert, issued Sept. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979), incorporated by reference herein.

The compositions of the present invention can also be administered topically to a biologic subject, i.e., by the direct laying on or spreading of the composition on epidermal or epithelial tissue. Such compositions include lotions, creams, solutions, gels and solids. These topical compositions comprise a safe and effective amount, usually at least about 0.5%, and preferably from about 1% to about 2%, of the alkadienamide.

Suitable carriers for topical administration of the alkadienamide preferably remain in place on the skin as a continuous film and resist being washed off easily by perspiration or by immersion in water. Generally, the carrier is organic in nature and capable of having dispersed or dissolved therein the alkadienamide. The carrier may include pharmaceutically-acceptable emollients, emulsifiers, thickening agents, and solvents.

Specific systemic and topical formulations useful in this invention are described in the following U.S. patent applications, all incorporated by reference herein: Ser. No. 359,464, LaHann, et al., filed Mar. 18, 1982 now U.S. Pat. No. 4,424,206; issued Jan. 3, 1984; Ser. No. 360,953, Buckwalter, et al., filed Mar. 23, 1982 now U.S. Pat. No. 4,401,663, issued Aug. 30, 1983; Ser. No. 381,672, Buckwalter, et al., filed May 25, 1982 now U.S. Pat. No. 4,460,602, issued July 17, 1984; and Ser. No. 384,685, Buckwalter, et al., filed June 3, 1982 now U.S. Pat. No. 4,443,473, issued Apr. 17, 1984. Topical vehicles, useful herein, are disclosed in the following U.S. patent applications, incorporated by reference herein: "Improved Penetrating Topical Pharmaceutical Compositions Containing 1-dodecylazacycloheptan-2-one", Ser. No. 560,275, Cooper, filed June 21, 1983; and "Penetrating Topical Pharmaceutical Compositions Containing N-(2-hydroxyethyl)-pyrrolidone", Ser. No. 506,273, Cooper, filed June 21, 1983. Additional formulations, useful for parenteral, oral, and topical administration of alkadienamides, are disclosed in the following U.S. patent applications concurrently filed herewith, all incorporated by reference herein: "Compositions Useful for Producing Analgesia", Ser. No. 514,206, filed July 14, 1983, LaHann and Buckwalter; "Novel Compounds and Compositions Useful for Producing Analgesia", Ser. No. 514,204, filed July 14, 1983, Janusz and LaHann; and "Novel Compounds and Compositions Useful for Producing Analgesia", Ser. No. 514,205, filed July 14, 1983, Janusz, Buckwalter and LaHann.

METHODS FOR PRODUCING ANALGESIA

The present invention also encompasses methods of producing analgesia in humans or lower animals through administering, to the human or lower animal, a safe and effective amount, usually from about 1 mg to about 3600 mg per day, preferably from about 200 mg to about 2000 mg per day, of an alkadienamide. While dosages higher than the foregoing are effective to produce analgesia, care must be taken in some individuals to prevent adverse side effects. The alkadienamides and compositions of this invention can be used to treat and prevent pain, and to provide analgesia in various disorders at the deeper structures, muscles, tendons, bursa and joints associated with disease and trauma, and in various other conditions in which compounds such as aspirin, codeine, and morphine have heretofore been used to alleviate pain and discomfort.

The alkadienamides and compositions of the instant invention can be administered topically or systemically. Systemic application includes any method of introducing the alkadienamide into the tissues of the body, e.g., intrathecal, epidural, intramuscular, transdermal, intravenous, intraperitoneal, subcutaneous, sublingual, and oral administration.

A preferred method of parenteral administration is through intramuscular injection. As is known and practiced in the art, all formulations for parenteral administration must be sterile. For mammals, especially humans, (assuming an approximate body weight of 70 kg) individual doses of from about 2 mg to about 400 mg of alkadienamide are acceptable. Individual doses of from about 50 mg to about 200 mg are preferred.

A preferred method of systemic application of the alkadienamides is through oral administration. For mammals, especially humans, (assuming an approximate body weight of 70 kg) individual doses of from about 1 mg to about 900 mg of alkadienamide are acceptable. Individual doses of from about 50 mg to about 600 mg are especially preferred.

Topical administration can be used to produce local or systemic analgesia, through directly laying on or spreading a safe and effective amount of the alkadienamide, or composition containing an alkadienamide, on epidermal or epithelial tissue, including outer skin and oral, gingival, and nasal tissue. The amount of alkadienamide to be topically administered depends upon such factors as the sensitivity, type and location of tissue to be treated, the composition and carrier (if any) to be administered, and the particular alkadienamide to be administered as well as the particular disorder to be treated and the extent to which systemic (as distinguished from local) analgesic effects are desired. The extent of systemic analgesia also depends upon such factors as the amount of alkadienamide, the area of tissue to be covered, and the ability of the alkadienamide composition to penetrate the skin tissues.

The following non-limiting Examples illustrate the compositions, processes, and uses of the present invention.

EXAMPLE I

N-vanillyl-(E,E)-9,12-octadecadienamide was synthesized by the following method:

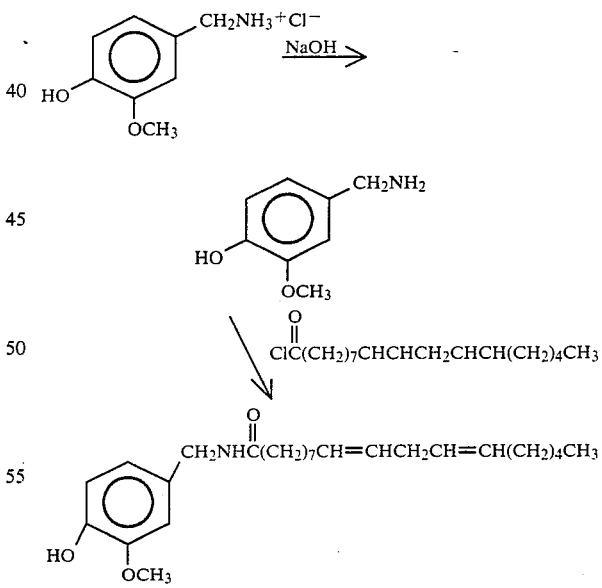

Specifically, 6.88 g of 4-hydroxy-3-methoxybenzylamine-HCl was dissolved in 50 ml of tetrahydrofuran (THF), and stirred. Added were 14 ml of a 5N solution of NaOH, and the mixture was stirred for 10 to 15 minutes. Then 10.6 g of (E,E)-9,12 octadecadienoyl chloride (linoelaidoyl chloride), dissolved in THF, was added dropwise. The mixture was then stirred overnight, allowing it to come to room temperature. The solvent was evaporated and the residue partitioned between ethyl ether and water. The organic phase extract was washed with HCl, sodium bicarbonate, water, and brine, and then dried and filtered. 16 g of crude N-vanillyl-(E,E)-9,12)-octadecadienamide was obtained. Purification by recrystallization from ether and pentane gave 9.4 g of analytically pure product. Its structure was confirmed via nuclear magnetic resonance and infrared spectroscopy.

In the above example, (Z,Z)-9,12-octadecadienoyl chloride, (Z,E)-9,12-octadecadienoyl chloride, (Z,E)-9,11-octadecadienoyl chloride, (E,E)-10,13-nonadecadienoyl chloride, and (E,E)-11,14-cosadienoyl chloride are substituted, respectively, for (E,E)-9,12-octadecadienoyl chloride, thereby obtaining each respective N vanillyl-alkadienamide.

EXAMPLE II

An analgesic composition, according to the present invention, was made comprising:

| | |
|---|---|
| N—vanillyl-(E,E)-9,12-octadecadienamide | 127.2 mg |
| ethanol | 0.75 ml |
| pyrrolidone | 0.75 ml |

The composition was made by simple dissolution of the alkadienamide in the liquid solvents. A mouse weighing 30 g, was injected subcutaneously with 0.1 ml of the composition, producing analgesia.

EXAMPLE III

A composition, according to the instant invention, for parenteral administration, is made with the following ingredients:

| | |
|---|---|
| N—vanillyl-(E,E)-9,12-octadecadienamide | 100 mg/ml of carrier |
| carrier (percent-by-weight): | |
| propylene glycol | 72% |
| polyethylene glycol | 17% |
| water | 10% |
| benzyl alcohol | 1% |

The alkadienamide is dissolved in the carrier and a human subject, weighing 70 kg, is injected subcutaneously with 1.0 ml of the composition thereby prepared, producing analgesia. At eight-hour intervals, two more subcutaneous injections are made, of 1.0 ml of the composition per administration, for a total of 300 mg N-vanillyl-(E,E)-9,12-octadecadienamide administered over a twenty-four-hour period.

In the above example, N-vanillyl-(Z,Z)-9,12-octadecadienamide, N-vanillyl-(Z,E)-9,12-octadecadienamide, N-vanillyl-(Z,E)-9,11-octadecadienamide, N-vanillyl-(E,E)-10,13-nonadecadienamide, N-vanillyl-(Z,Z)-11,14-eicosadienamide, and N-vanillyl-(E,E)-11,14-eicosadienamide are substituted, respectively, for N-vanillyl-(E,E)-9,12-octadecadienamide, with substantially similar results.

EXAMPLE IV

A composition, according to the instant invention, for parenteral administration, is made with the following components:

| | |
|---|---|
| N—vanillyl-(E,E)-9,12-octadecadienamide | 100 mg/ml of carrier |
| carrier (percent-by-weight): | |
| sesame oil | 98% |
| benzyl alcohol | 2% |

A human subject, weighing 70 kg, is injected via deep-intramuscular injection, with 1.0 ml of the composition prepared above, producing analgesia.

In the above example, N-vanillyl-(Z,Z)-9,12-eicosadienamide, 15-hydroxy-N-vanillyl-(Z,Z)-9,12-octadecadienamide, N-vanillyl-(E,E)-9,12-octadecadienethioamide, and N-[(3,4-dihydroxyphenyl)methyl]-(E,E)-9,12-octadecadienamide and are substituted, respectively, for N-vanillyl-(E,E)-9,12-octadecadienamide, with substantially similar results.

EXAMPLE V

A composition, according to the instant invention, for parenteral administration, is made with the following components:

| | |
|---|---|
| N—vanillyl-(Z,Z)-9,12-octadecadienamide | 100 mg/ml of carrier |
| carrier: sodium citrate buffer with (percent-by-total weight): | |
| lecithin | 0.48% |
| carboxymethylcellulose | 0.53% |
| povidone | 0.50% |
| methyl paraben | 0.11% |
| propyl paraben | 0.011% |

The above ingredients are admixed, forming a suspension. A human subject, weighing approximately 70 kg, is injected, via intramuscular injection, with 2.0 ml of the composition formed above, producing analgesia.

EXAMPLE VI

A composition, according to the instant invention, for parenteral administration, is made by admixing the following components:

| | |
|---|---|
| N—[(4-acetoxy-3-methoxyphenyl)methyl]-(E,E)-9,12-octadecadienamide | 100 mg/ml of carrier |
| carrier (percent by weight): | |
| ethyl oleate | 98.0% |
| benzyl alcohol | 2.0% |

A human subject, weighing 70 kg, is injected via intramuscular injection, with 2.0 ml of the composition prepared above, producing analgesia.

In the above example, N-[(4-butoxy-3-methoxyphenyl)methyl]-(E,E)-9,12-octadecadienamide is substituted for N-[(4-acetoxy-3-methoxyphenyl)methyl]-(E,E)-9,12-octadecadienamide, with substantially similar results.

EXAMPLE VII

A composition, according to the instant invention, is made with the following components:

| | |
|---|---|
| N—vanillyl-(E,E)-9,12-octadecadienamide | 2000 mg |
| sesame oil | 50 ml |
| benzyl alcohol | 6 ml |
| 8% gelatin in water | 100 ml |

| | |
|---|---|
| tartaric acid | 60 mg |

The alkadienamide is dissolved in the sesame oil and benzyl alcohol. An emulsion is obtained through adding this solution to a mixture of the gelatin and tartaric acid. This emulsion is administered orally to a human subject, weighing approximately 70 Kg, producing analgesia.

EXAMPLE VIII

A composition, according to the instant invention, for oral administration, is made with the following components:

| | |
|---|---|
| N—vanillyl-(E.E)-10,13-nonadecadienamide | 100 mg/ml of carrier |
| carrier (percent-by-weight): | |
| propylene glycol | 100% |

5.0 ml of the syrup thereby prepared is administered orally to a human subject, producing analgesia.

In the above example, flavoring agents, sweetening agents such as sucrose, lactose, mannitol and saccharin, and preservatives such as glycerin, methyl paraben, propylparaben, benzoic acid, sodium benzoate and alcohol, are added, singly or in combination, to the composition formed above, with substantially similar results.

EXAMPLE IX

A composition, according to the instant invention, for oral administration, is made with the following components:

| | |
|---|---|
| N—vanillyl-(Z,Z)-11,14-eicosadienamide | 100 mg/ml of carrier |
| carrier (percent by weight): | |
| cottonseed oil | 99% |
| benzyl alcohol | 1% |

Soft gelatin capsules, each having a volume of 0.3 ml, are filled with the composition formed above. Two capsules are administered to a human subject every eight hours, producing sustained analgesic effects.

EXAMPLE X

A composition, according to the instant invention, for oral administration, is made with the following components:

| Component | Bulk | Individual Tablet |
|---|---|---|
| N—vanillyl-(E,E)-9,12-octadecadienamide | 70 g | 350 mg |
| starch | 6 | 30 |
| magnesium stearate | 1 | 5 |
| microcrystalline cellulose | 20 | 100 |
| colloidal silicon dioxide | 0.5 | 2.5 |
| povidone | 2.5 | 12.5 |

The above ingredients are admixed into a bulk mixture, totalling 100 g. Compressed tablets are formed, using tabletting methods known in the art, each containing 0.5 g of the bulk mixture. A human subject, weighing approximately 70 kg, is orally administered two of the tablets, for a total dose of 700 mg of alkadienamide, producing analgesia.

EXAMPLE XI

A composition, according to the instant invention, for oral administration, is made with the following components:

| Component | Bulk | Individual Tablet |
|---|---|---|
| N—vanillyl-(Z.Z)-9,12-octadecadienamide | 100 g | 500 mg |
| mannitol | 97.2 | 486 |
| acacia | 5.86 | 29.3 |
| starch | 9.62 | 48.1 |
| talc | 3.2 | 16.0 |
| calcium stearate | 0.42 | 2.1 |
| orange flavor mix | 1.06 | 5.3 |

The above ingredients are admixed into a bulk mixture totalling 217.4 g. Chewable tablets are formed, using tabletting methods known in the art, each containing 1.09 g of the bulk mixture, for a total of 200 tablets formed. A human subject, weighing approximately 70 kg, is orally administered three of the tablets, for a total dose of 1500 mg of alkadienamide, producing analgesia.

EXAMPLE XII

A composition, according to the instant invention, for oral administration, is made with the following components:

| | |
|---|---|
| N—vanillyl-(E,E)-9,12-octadecadienamide | 1000 mg |
| starch | 10.2 |
| magnesium stearate | 5.1 |

A capsule is made by filling with the above ingredients, and administered to a human subject, weighing approximately 70 kg, producing analgesia.

EXAMPLE XIII

A lotion composition, according to the instant invention, for topical administration, is formed through admixing the following components (percentages-by-weight):

| | |
|---|---|
| N—vanillyl-(E,E)-11,14-eicosadienamide | 2.0% |
| isopropyl myristate | 8.0% |
| corn oil | 5.0% |
| propylene glycol | 5.0% |
| triethanolamine oleate | 5.0% |
| xanthan gum | 0.5% |
| water | 74.5% |

Approximately 4 ml of the lotion formed is applied to a 80 cm$^2$ portion of the skin of a human subject, producing analgesia.

In the above example, 15-methyl-N-vanillyl-(Z,Z)-9,12-octadecadienamide and 15-ethyl-N-vanillyl-(Z,Z)-9,12-octadecadienamide are substituted for N-vanillyl-(E,E)-11,14-eicosadienamide respectively, with substantially similar results.

EXAMPLE XIV

An ointment composition, according to the instant invention, for topical administration, is formed with the following components (percentages-by-weight):

| | |
|---|---|
| N—vanillyl-(E.E)-9,12-octadecadienamide | 2.0% |

| -continued | |
|---|---|
| oleyl alcohol | 30.0% |
| cetyl alcohol | 40.0% |
| propylene glycol | 28.0% |

The components are admixed and approximately 6 ml of the ointment is applied to a 100 cm² portion of the skin of a human subject, producing analgesia.

What is claimed is:

1. Alkadienamide compounds, and pharmaceutically-acceptable salts thereof, of the formula:

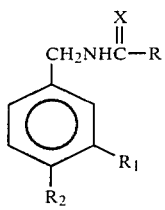

wherein X is O or S; R is straight or branched diene having from 11 to 23 carbon atoms, the stereochemistry of said diene being ZE, EZ, or EE; $R_1$ is H, OH, or $OCH_3$; $R_2$ is OH or a short-chain ester; and wherein at least one of $R_1$ and $R_2$ is OH or $OCH_3$.

2. Alkadienamide compounds, and pharmaceutically-acceptable salts thereof, according to claim 1, wherein $R_1$ is $OCH_3$ and $R_2$ is OH.

3. Alkadienamide compounds, and pharmaceutically-acceptable salts thereof, according to claim 1, wherein $R_2$ is a shortchain ester.

4. Alkadienamide compounds, and pharmaceutically-acceptable salts thereof, according to claim 2, selected from the group consisting of N-vanillyl-(Z,E)-9,12-octadecadienamide, N-vanillyl-(E,E)-9,12-octadecadienamide, N-vanillyl-(Z,E)-9,11-octadecadienamide, N-vanillyl-(E,E)-10,13-nonadecadienamide, and N-vanillyl-(E,E-11,14-eicosadienamide.

5. The alkadienamide compound and pharmaceutically-acceptable salts thereof, according to claim 3, wherein said alkadienamide is N-[(4-acetoxy-3-methoxyphenyl)methyl]-(E,E)-9,12-octadecadienamide.

6. The alkadienamide compound N-vanillyl-(Z,Z)-11,14-eicosadienamide, and pharmaceutically-acceptable salts thereof.

7. A composition for producing analgesia in humans or lower animals, comprising:
(a) a safe and effective amount of an alkadienamide compound or pharmaceutically-acceptable salt thereof, or mixtures thereof, of the formula:

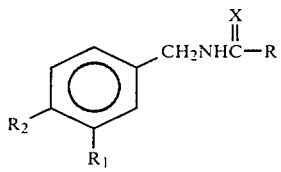

wherein X is O or S, R is straight or branched diene having from 11 to 23 carbon atoms, $R_1$ is H, OH, or $OCH_3$, $R_2$ is OH or a short-chain ester, and wherein at least one of $R_1$ and $R_2$ is OH or $OCH_3$; and
(b) a pharmaceutically-acceptable carrier.

8. A composition, according to claim 7, wherein R is straight or branched diene having from 16 to 21 carbon atoms.

9. A composition, according to claim 7, wherein $R_1$ is $OCH_3$ and $R_2$ is OH.

10. A composition, according to claim 7, wherein $R_2$ is a shortchain ester.

11. A composition, according to claim 7, comprising a pharmaceutically-acceptable salt of said alkadienamide compound, selected from the group consisting of sodium, potassium, calcium, magnesium, and ammonium salts.

12. A composition, according to claim 8, for parenteral administration, comprising at least about 90%, by weight, of said pharmaceutically-acceptable carrier.

13. A composition, according to claim 8, for oral administration, comprising from about 25% to about 50%, by weight, of said alkadienamide.

14. A composition, according to claim 9, wherein said alkadienamide compound is selected from the group consisting of N-vanillyl-(Z,Z)-9,12-octadecadienamide, N-vanillyl-(Z,E)-9,12-octadecadienamide, N-vanillyl-(E,E)-9,12-octadecadienamide, N-vanillyl-(Z,E)-9,11-octadecadienamide, N-vanillyl-(E,E)-10,13-nonadecadienamide, N-vanillyl-(Z,Z)-11,14-eicosadienamide, and N-vanillyl-(E,E)-11,14-eicosadienamide, and pharmaceutically-acceptable salts thereof and mixtures thereof.

15. A composition, according to claim 10, wherein said alkadienamide compound is N-[(4-acetoxy-3-methoxyphenyl)methyl]-(E,E)-9,12-octadecadienamide.

16. A composition, according to claim 14, wherein said alkadienamide compound is N-vanillyl-(E,E)-9,12-octadecadienamide.

17. A method for producing analgesia in humans or lower animals, which comprises administering to said human or lower animal a safe and effective amount of an alkadienamide compound or pharmaceutically-acceptable salt thereof, or mixtures thereof, of the formula:

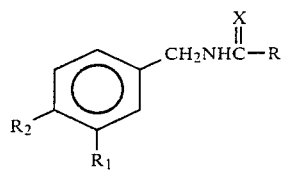

wherein X is O or S; R is straight or branched diene having from 11 to 23 carbon atoms; $R_1$ is H, OH, or $OCH_3$; $R_2$ is OH, or a short-chain ester; and wherein at least one of $R_1$ and $R_2$ is OH or $OCH_3$.

18. A method, according to claim 17 wherein R of said alkadienamide compound is straight or branched diene having from 16 to 21 carbon atoms.

19. A method, according to claim 18 wherein said alkadienamide compound is selected from the group consisting of N-vanillyl-(Z,Z)-9,12-octadecadienamide, N-vanillyl-(Z,E)-9,12-octadecadienamide, N-vanillyl-(E,E)-9,12-octadecadienamide, N-vanillyl-(Z,E)-9,11-octadecadienamide, N-vanillyl-(E,E)-10,13-nonadecadienamide, N-vanillyl-(Z,Z)-11,14-eicosadienamide, N-vanillyl-(E,E)-11,14-eicosadienamide, N-[(4-acetoxy-3-methoxyphenyl)methyl]-(E,E)-9,12-octadecadienamide, and pharmaceutically-acceptable salts thereof and mixtures thereof.

20. A method, according to claim 18, wherein said alkadienamide is administered intramuscularly.

21. A method, according to claim 18, for producing analgesia in humans or lower animals, wherein said alkadienamide is administered orally.

22. A method, according to claim 18, for producing analgesia in humans or lower animals, wherein said alkadienamide is administered topically.

* * * * *